(12) United States Patent
Horn (10) Patent No.: US 8,423,123 B2
(45) Date of Patent: Apr. 16, 2013

(54) SYSTEM AND METHOD FOR IN-VIVO FEATURE DETECTION

(75) Inventor: Eli Horn, Kiryat Motzkin (IL)

(73) Assignee: Given Imaging Ltd., Yoqneam (IL)

( * ) Notice: Subject to any disclaimer, the term of this patent is extended or adjusted under 35 U.S.C. 154(b) by 1812 days.

(21) Appl. No.: 11/239,392

(22) Filed: Sep. 30, 2005

(65) Prior Publication Data

US 2007/0078335 A1    Apr. 5, 2007

(51) Int. Cl.
*A61B 5/05*    (2006.01)

(52) U.S. Cl.
USPC ........... 600/425; 382/130; 382/131; 382/128; 600/407; 600/410; 348/65; 345/419; 345/440; 345/589

(58) Field of Classification Search .......... 345/440, 345/589; 715/764, 716; 348/65; 600/407, 600/408, 425; 324/306, 318
See application file for complete search history.

(56) References Cited

U.S. PATENT DOCUMENTS

| | | | |
|---|---|---|---|
| 3,683,389 A | 8/1972 | Hollis | |
| 3,888,237 A | 6/1975 | Mori | |
| 3,971,362 A | 7/1976 | Pope et al. | |
| 4,278,077 A | 7/1981 | Mizumoto | |
| 4,689,621 A | 8/1987 | Kleinberg | |
| 4,741,327 A | 5/1988 | Yabe | |
| 4,844,076 A | 7/1989 | Lesho et al. | |
| 4,915,113 A | 4/1990 | Holman | |
| 5,279,607 A | 1/1994 | Schentag et al. | |
| 5,421,337 A | 6/1995 | Richards-Kortum et al. | |
| 5,604,531 A | 2/1997 | Iddan et al. | |
| 5,819,736 A | 10/1998 | Avny et al. | |
| 5,833,603 A | 11/1998 | Kovacs et al. | |
| 5,853,005 A | 12/1998 | Scanlon | |
| 6,010,453 A | 1/2000 | Fiddian-Green | |
| 6,074,349 A | 6/2000 | Crowley | |
| 6,165,128 A | 12/2000 | C'espedes et al. | |
| 6,240,312 B1 | 5/2001 | Alfano et al. | |
| 6,266,550 B1 | 7/2001 | Selmon et al. | |
| 6,285,897 B1 | 9/2001 | Kilcoyne et al. | |

(Continued)

FOREIGN PATENT DOCUMENTS

| | | |
|---|---|---|
| DE | 34 40 177 | 5/1986 |
| EP | 1 260 176 | 11/2002 |

(Continued)

OTHER PUBLICATIONS

Zigang Wang, Bin Li, and Zhenrong Liang; "Feature-Based Texture Display for Detection of Polyps on Flattened Colon Vojume", Proceedings of the 2005 IEEE (Engineering in Medicine and Biology 27th Annual Conference), Shanghai, China, Sep. 1-4, 2005; pp. 1-4.*

(Continued)

*Primary Examiner* — Tse Chen
*Assistant Examiner* — Baisakhi Roy
(74) *Attorney, Agent, or Firm* — Pearl Cohen Zedek Latzer, LLP (57) ABSTRACT

An in-vivo imaging system and method to screen for colorectal polyps in the GI tract may include an in-vivo imaging device for capturing a stream of image frames in a GI tract, a polyp detector for detecting and/or identifying one or more image frames from the stream of image streams that may show colorectal polyps, and a graphical user interface (GUI) to display image frames detected.

18 Claims, 4 Drawing Sheets

U.S. PATENT DOCUMENTS

| | | | |
|---|---|---|---|
| 6,475,145 | B1 | 11/2002 | Baylor |
| 6,549,796 | B2 | 4/2003 | Sohrab |
| 6,904,308 | B2 | 6/2005 | Frisch et al. |
| 7,454,045 | B2 * | 11/2008 | Yao et al. .................. 382/128 |
| 7,480,401 | B2 * | 1/2009 | Shen et al. .................. 382/131 |
| 2001/0035902 | A1 | 11/2001 | Iddan et al. |
| 2001/0051766 | A1 | 12/2001 | Gazdzinski |
| 2002/0042562 | A1 | 4/2002 | Meron et al. |
| 2002/0097320 | A1 | 7/2002 | Zalis |
| 2003/0013370 | A1 | 1/2003 | Glukhovsky |
| 2003/0167000 | A1 | 9/2003 | Mullick et al. |
| 2005/0075551 | A1 | 4/2005 | Horn et al. |
| 2005/0078858 | A1 * | 4/2005 | Yao et al. .................. 382/128 |
| 2005/0096712 | A1 | 5/2005 | Abraham-Fuchs et al. |
| 2006/0164511 | A1 * | 7/2006 | Krupnik .................. 348/65 |
| 2006/0247514 | A1 * | 11/2006 | Panasyuk et al. .................. 600/410 |
| 2007/0024946 | A1 * | 2/2007 | Panasyuk et al. .................. 359/253 |
| 2009/0244260 | A1 * | 10/2009 | Takahashi et al. .................. 348/45 |

FOREIGN PATENT DOCUMENTS

| | | |
|---|---|---|
| JP | 57-45833 | 3/1982 |
| JP | 3-289779 | 12/1991 |
| JP | 4109927 | 4/1992 |
| JP | 4-180736 | 6/1992 |
| JP | 5015515 | 1/1993 |
| JP | 6142081 | 5/1994 |
| JP | 2001224553 | 8/2001 |
| WO | WO 92-21307 | 12/1992 |
| WO | WO 98/11816 | 3/1998 |
| WO | WO 01-08548 | 2/2001 |
| WO | WO 01-50941 | 7/2001 |
| WO | WO 01-53792 | 7/2001 |
| WO | WO 01-87377 | 11/2001 |
| WO | WO 2004/058041 | 7/2004 |
| WO | WO 2005/062715 | 10/2005 |

OTHER PUBLICATIONS

U.S. Appl. No. 10/879,053, filed Jun. 30, 2004, Horn.
U.S. Appl. No. 60/235,583, filed Sep. 27, 2000, Meron.
U.S. Appl. No. 60/311,351, filed Aug. 13, 2001, Meron et al.
European Search Report for European Application No. EP 06 12 1330 completed on Mar. 13, 2007.
Office Action for European Patent Application No. 06121330.2 dated Jun. 18, 2010.
F. Vilariño, P. Spyridonous, J. Vitria, F. Azpiroz , P. Radeva, "*Cascade analysis for intestinal contraction detection*", CARS'2006, Osaka, Japon, 2006, pp. 9-10.
Panagiota Spyridonos, Fernando Vilariño, Jordi Vitrià, Petia Radeva, "*Identification of Intestinal Motility Events of Capsule Endoscopy Video Analysis*", In Lecture Notes in Computer Science, Publisher: Springer Berlin / Heidelberg ISSN: 0302-9743. vol. 3708 / 2005, (ISI 0,402).

* cited by examiner

SYSTEM AND METHOD FOR IN-VIVO FEATURE DETECTION

FIELD OF THE INVENION

The present invention relates to an in-vivo imaging device, system, and method to screen for the presence of polyps along a body lumen.

BACKGROUND OF THE INVENTION

Polyps, abnormal growths or tumors that may project from a mucous membrane, for example the body lumen wall of the nose, gastrointestinal (GI) tract, and the uterus may be known to occur and in some cases may be an important precursor to cancer Colorectal polyps found in the colon or rectum of the GI tract may be known to be a precursor for colorectal cancer. The known long pre-malignant stadium of colorectal cancer and the known high survival rate after polyp removal may enable efficient prevention of colorectal cancer by systematic screening and timely removal of colorectal polyps. Manual screening procedures or methods, for example, screening procedures to screen for colorectal polyps found in the colon or rectum are known.

Manual polyp screening methods may include imaging a body lumen wall, for example, the entire length of the colon or the entire GI tract with a stream of image frames and manually reviewing the stream to detect and/or identify in one or more image frames showing any visible morphologic changes to the membrane of the body lumen wall.

Devices and systems for performing in-vivo imaging, for example, of body lumen walls are known in the art. Such devices may include, inter alia, various endoscopic imaging systems, computed tomography (CT) devices, and x-ray imaging devices.

Typically, the stream of image frames captured during a screening procedure, for example a colorectal polyps screening procedure may be lengthy so as to covet substantially the entire area of the colon and rectum. Manually reviewing all image frames may be tedious as well as undesirable and inefficient as a quick screening procedure to indicate the presence of polyps or to indicate the probability that polyps may be present in a body lumen. In addition, the visibility of a polyp may be subtle and a health professional may miss the occurrence of one or more polyps when reviewing a lengthy stream of image flames.

Known polyp screening procedures typically require cleansing preparation and insufflation. Insufflation may stretch and flatten a polyp so that it may be difficult to detect a polyp. In addition, the cleansing preparation and insufflation may be unpleasant for the patient and may result in patients avoiding undergoing such a procedure.

SUMMARY OF THE INVENTION

An embodiment of the system and method of the present invention may enable automatic screening of polyps along a body lumen. According to one embodiment of the present invention, at least one image frame, for example stream of image fumes may be captured, for example, by an autonomous imaging device. The presence of a predetermined geometric form, for example a substantially elliptical form, visible in the captured stream of images may be automatically detected by a polyp detector and may be classified based on at least one predetermined parameter, for example based on the color, size, and/or shape of the identified form. Scores may be assigned to individual image frames based on the number of identified forms detected in each image frame and based on its classification. Candidate image frames may be selected based on the scoring and may be displayed to a user.

BRIEF DESCRIPTION OF THE DRAWINGS

The present invention will be understood and appreciated more fully from the following detailed description taken in conjunction with the drawings in which.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

The colorectal polyp may be an important precursor to colon cancer. This benign lesion typically may protrude from the wall as a small, sloped mound and may be seen in a two dimensional image as a circular or elliptical form. Other identifying features may be used to identify a polyp. The known long pre-malignant stadium and the known high survival rate after polyp removal may enable efficient prevention of colon cancer by systematic screening and timely removal of colorectal polyps.

Embodiments of the present invention, describe a system, and method for screening for colorectal polyps, for example by providing a system, and method for automatically, without a user intervention, identifying, detecting, selecting, and marking image flames captured in the GI tract that may indicate the presence of colorectal poylps. The selected image frames may be displayed to a health professional for diagnosis. According to one embodiment of the present invention, an autonomous in-vivo imaging device, for example an imaging device in the form of a swallowable capsule, may capture a series of image flames of a body lumen as well as other information from within or along a body lumen and may transmit the captured images and other information to one or more external units. Analysis of the transmitted data may be used to automatically and/or machine select and mark image frames that may be candidates for polyp identification Analysis and processing of the data may be performed automatically without user intervention. Machine selection, detection and/or marking of image frames that may be candidates for polyp identification may be performed at least partially by a polyp detector and such that user intervention in the detection of image flames that may be candidates for polyp identification may not be required. Machine selection, detection an/or marking may be performed by, for example, one or more processors, a workstation, circuitry, a sensor or any other computation and/or sensing able device. Selected images may be displayed to a health professional for diagnosis. In some embodiments of the present invention, screening may also be facilitated with data that may be partially occluded by content For example, image frames may be captured in an environment that may be partially occluded with content, for example content that may be present within a body lumen, e.g. colon.

Figure 1:
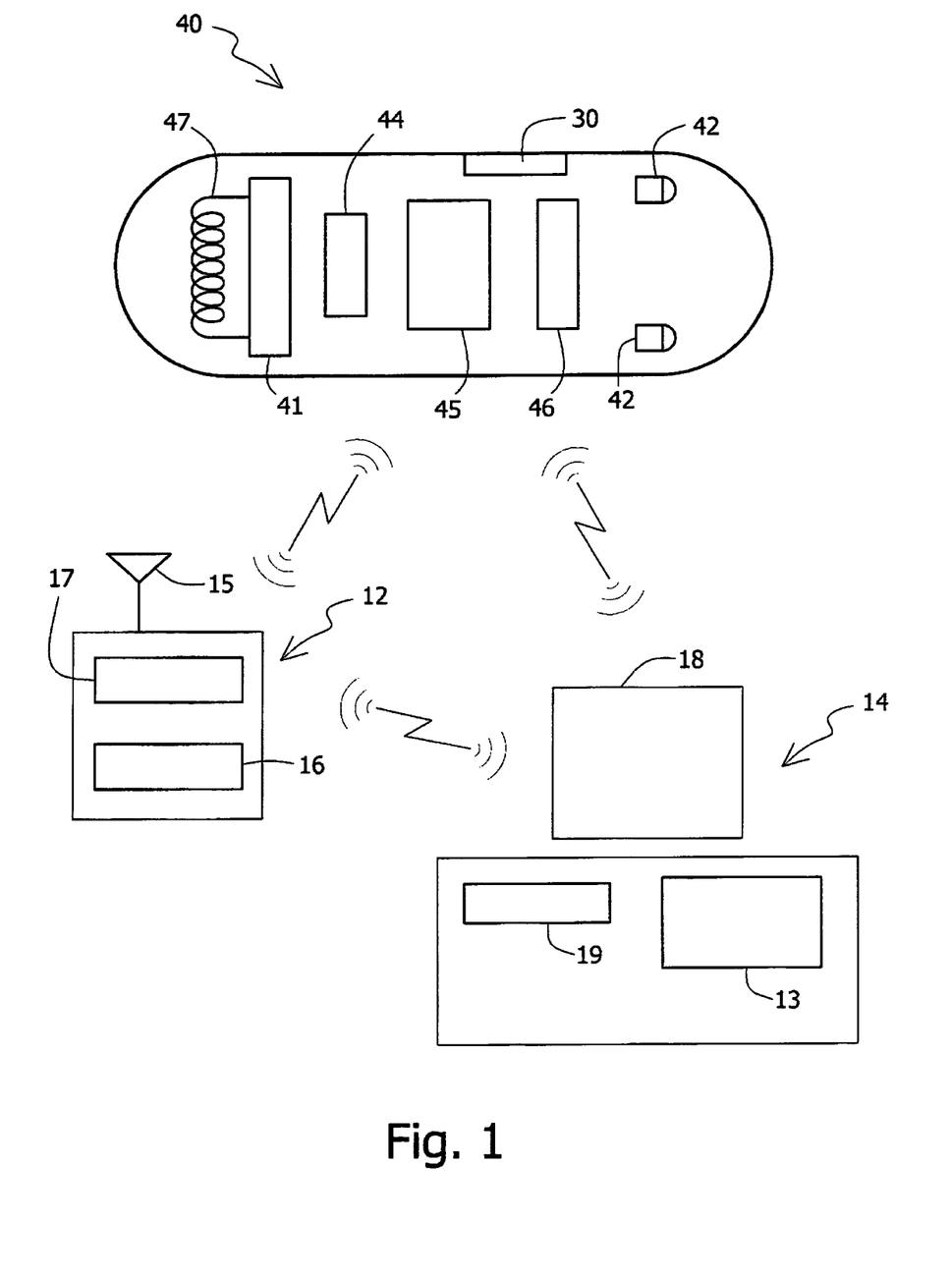
FIG. 1 shows schematic illustration of an in-vivo imaging system according to an embodiment of the present invention.

Reference is made to FIG. 1, which shows a schematic diagram of an in-vivo imaging system according to an embodiment of the present invention. Typically, the in-vivo imaging system may include an in-vivo imaging device 40, an external receiving device and/or recording device 12, e.g. data receiver, and a workstation 14. The in-vivo imaging device 40, may have an imager 46, for capturing image flames or a stream of image flames, an illumination source 42, for illuminating the body lumen, a power source 45 for powering device 40, a processor 44 for processing data and commands to and from device 40, and a transmitter 41 with antenna 47, for transmitting image and possibly other data to an external receiver 12. In some embodiments of the present invention, in-vivo device 40 may include one or more sensors 30, in addition to imager 46, for example, temperature sensors, pH sensors, pressure sensors, blood sensors, tracking sensors, etc. Imager 46 may be a CCD or CMOS imager, or may be another solid state imaging device or other imaging device. Illumination source 42 may include one or mole LEDs or other illumination sources. In some embodiments of the present invention, device 40 may be an autonomous device, a capsule, or a swallowable capsule. In other embodiments of the present invention, device 40 may not be autonomous, for example, device 40 may be an endoscope or other in-vivo imaging device.

The in-vivo imaging device 40 may typically, according an embodiment of the present invention, transmit information (e.g., images or other data) to an external receiver 12 possibly close to or worn on a subject. Typically, the receiver 12 may include an antenna or antenna array 15 and a data receiver storage unit 16. Typically antenna array 15 may pick up signals transmitted by device 40 or the transmitter 41 and antenna 47 of device 40. The external receiver 12 may include one or more processors 17 for processing image data or other data. Receiver 12 may include a tracking unit 11, for tracking the location of an autonomous in-vivo imaging device 40 over time. For example, tracking unit 11 may track the location of device 40 in three dimensional space over time and/or may track the distance, for example the distance over time that device 40 traveled through the GI tract or through a specific organ in the GI tract over time. Tracking unit 11 may be similar to various embodiments described, for example, in US Patent Application Publication No. US-2002-0173718-A1 published on Nov. 21, 2002 and U.S. patent application Ser. No. 10/879,053 filed on Jun. 30, 2004 all of which are assigned to the common assignee of the present application and incorporated herein by reference in their entirety. Other known tracking units or methods of tracking a device may be used. In other embodiments, the tracking unit 11 or part of its functionality may be included in device 40. The receiver 12 may take on other suitable configurations and may not include an antenna or antenna array. In one embodiment of the present invention, the receiver 12 may, for example, include a LCD display for displaying image data or other data, e.g., tracking data in other embodiments, receiver 12 may be electrically connected, e.g. via wire, blue tooth, or wireless connection, to a display unit, e.g. display unit 18 or workstation 14, to display data transmitted by in-vivo device 40 and/or processed by processing unit 17, 44, or workstation 14.

In one embodiment of the present invention, the receiver 12 may, for example, receive and store data from imaging device 40, e.g. an image stream data captured and/or processed by processor 17 and later transfer the received data to a workstation 14, such as a personal computer, laptop or other portable or stationary computing devices, where the data may be farther analyzed, stored, and/or displayed to a user, e.g. a health professional. Typically, workstation 14 may include processing unit 13, data processor storage unit 19, a disk drive, input-output devices, and display unit 18 e.g. a monitor, although alternate configurations are possible. Processing unit 13 may typically, as part of its functionality, act as a controller controlling the display of data for example, image data or other data. In one example, processor 13 and/or processor 17 may be employed to construct a polyp screening movie from candidate image frames selected by the poly detector. Display unit 18 may typically be a conventional video display, but may, in addition, be any other device capable of providing image or other data. Instructions or software for carrying out a method according to an embodiment of the invention may be included as part of workstation, for example stored in memory 19. A polyp detector may be included as part of the functionality of processor 13, processor 44 and/or processor 17 and may select from an image stream, one or more image frames that may be candidates for polyp identification, In another embodiment, poly detector may be included as part of the functionality of the solid state imaging device, e.g. imager 40. In yet another embodiment, polyp detector may be included as part of the functionality of an ASIC (application specific integrated circuit), for example and ASIC included in device 40. In one example, the polyp detector may be a series of commands or an algorithm that may be implemented to detect in one or more image frames, for example a stream of image frames, the presence of pre-determined features and/or parameters. Based on the detection, candidate image frames may be selected. Output from the polyp detector may be transferred to a display unit 18, a display unit included in receiver 12 and/or processing unit 13 or 17 by either wire or wireless communication.

In other embodiments, each of the various components need not be required; for example, the in-vivo device 40 may transmit or otherwise transfer (e.g, by wire) data marking image frames that may be candidates for polyp identification directly to a viewing device or workstation 14 In one embodiment of the present invention, device 40 may only transmit selected image frames that may be candidates for polyp identification.

In-vivo imaging systems suitable for use with embodiments of the present invention may be similar to various embodiments described, for example in U.S. Pat. No. 5,604,531, entitled "In-Vivo Video Camera System", assigned to the common assignee of the present application and incorporated herein by reference in its entirety, and/or US Patent Application Publication Number 20010035902 published on Nov. 1, 2001 and entitled "Device and System fox In-Vivo Imaging", also assigned to the common assignee of the present application and incorporated herein by reference in its entirety.

Other in-vivo systems, having other configurations, may be used. Of course, devices, systems, structures, functionalities and methods as described herein may have other configurations, sets of components, processes, etc.

In some embodiments of the present invention, an in-vivo image device 40 may be swallowed, or otherwise inserted within a gastrointestinal (GI) tract and may pass through the GI tract, for example, via natural peristaltic motion while capturing a series of image frames, e.g. capturing image frames periodically at two frames per second. In other embodiments of the present invention, the in-vivo imaging device may advance through the GI tract via other suitable means and may capture image frames at other suitable rates, for example, at variable rates. Image frames captured as well as other, data may be transmitted externally for processing and display. According to one embodiment of the present invention, tracking data, tracking the location of the in-vivo imaging device over time or over the course through the GI tract may be included in the processing and display of data. For example, tracking data may be used to indicate the point, e.g. the image frame, at which polyp screening should begin, e.g. the tracking system may detect entrance into the colon. Data captured may be processed to automatically select image frames that may be candidates for polyp diagnosis.

According to an embodiment of the present invention, the screening procedure with device 40 may be performed without previously requiring a patient to undergo a cleansing preparation that may be common in known colonoscopy procedures or other procedures. In some instances, images captured by device 40 may include content present in the body lumen that may partially occlude imaging along the body lumen walls.

Figure 2:
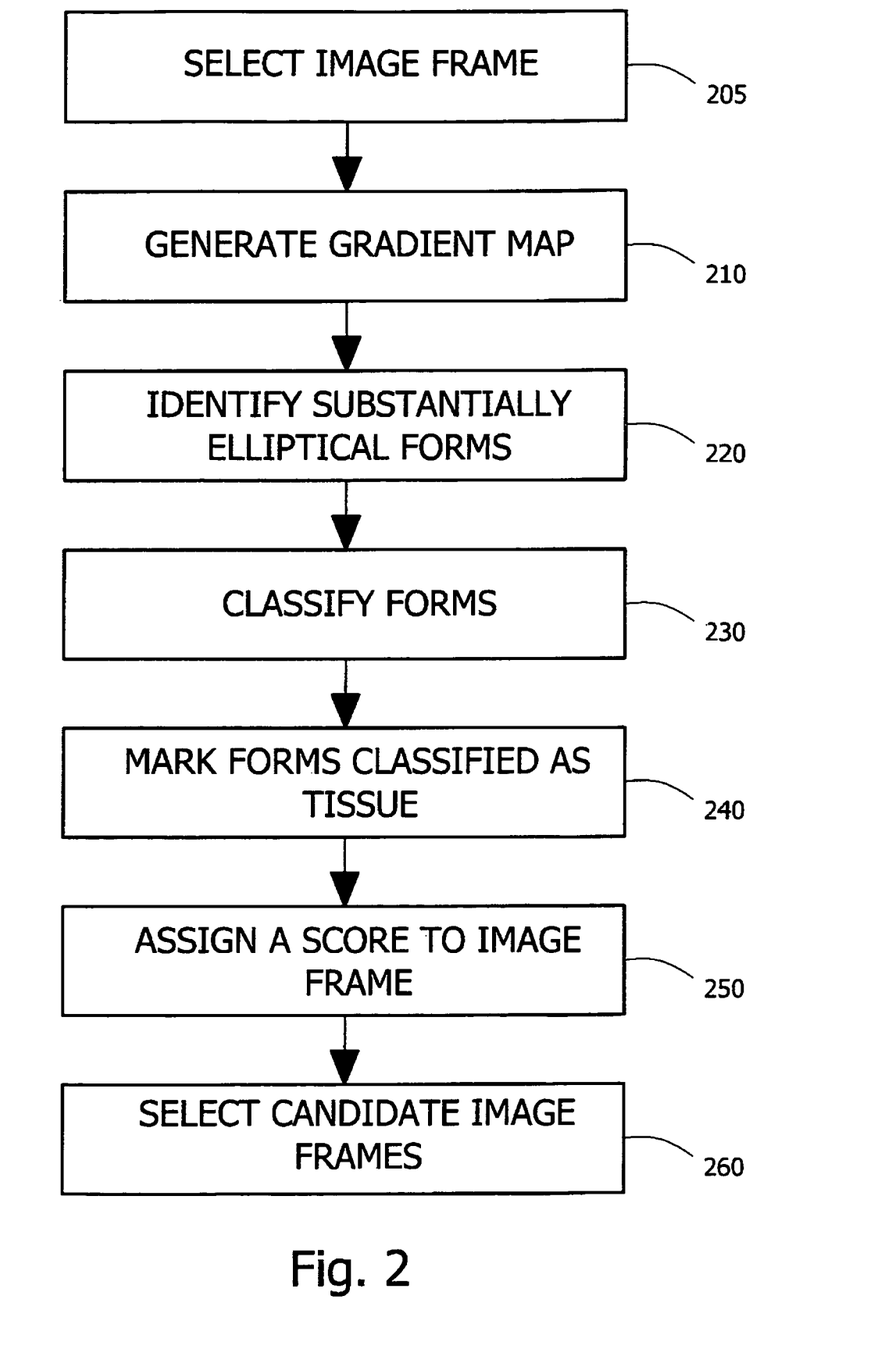
FIG. 2 is a flow chart describing a method for identifying potential polyp structures that may be visible in an image stream according to an embodiment of the present invention.

Reference is now made to FIG. 2 describing a method for automatic selection of image frames that may be candidates for polyp identification. Selection may be based on automatic detection of one or more geometric forms that may be polyp structures in an image frame, For example, colorectal polyps may appear in a two dimensional image as a substantially circular or elliptical shaped form. Other known morphologic features that may also appear as substantially elliptical forms in a two dimensional image may include, for example, content, or bubbles present within a body lumen In one embodiment of the present invention a polyp detector may search for substantially elliptical forms in an image frame and classify the forms based on at least one predetermined and/or predefined parameter, for example shape, size and/or color. For example, a polyp detector may search for substantially elliptical forms in an image frame and classify the forms as either tissue, e.g. polyp or as another form, e.g. content based on their shape, size and/or color. Other suitable predetermined and/or predefined geometrical forms may be detected and/or identified and other parameters for classifying the forms may be used. In one example, polyp screening may be performed on each of the individual image frames of the original image stream. In another embodiment, known motion tracking methods may be used to combine one or mote image frames that may show over lapping regions and polyp screening may be performed on the combined images.

According to one embodiment of the present invention, an image frame, for example an image frame captured by an in-vivo imaging device 40 along a body lumen may be selected (block 205) In one example, polyp screening may begin on the first image frame captured by the in-vivo device or the first image frame in the original image stream. In an alternate example, polyp screening may begin on the first image frame captured in a specific region of interest, for example polyp screening may be performed starting with the first image captured in the cecum, or colon. Position tracking methods, image analysis or data from various sensors may be used to identify the relevant image frame to be used or analyzed in the screening procedure. Other methods may be used A gradient map of the selected frame may be generated (block 210) by methods known in the art, for example, by implementing known Sobel or Canny filters. The generated gradient map may be used to identify, for example automatically identify without user intervention, the presence of one or more forms or structures that may have a substantially elliptical shape (block 220). For example, a Hough transform may be used to identify a substantially elliptical shape Other suitable methods may be used to identify an elliptical structure Typically elliptical shaped forms in the colon and rectum may have a high probability of being either content or a polyp. Parameters, such as dimensions and/or size of each form as well as the color may be used to differentiate between forms that may be content, polyps, of neither Identified ellipses and/or other forms may be classified and/or sorted, for example, as either content or a polyp based on analysis of for example, their size and color (block 230). For example identified forms may be sorted based on comparing the color of the forms to defined colors In one example, tissue color may be defined based on sample images taken, for example, by a pool or database of images taken from volunteers. In another example, tissue color may be defined per patient based on color in one of mote areas in an image frame and/or in one or more image frames. For example an area in an image frame identified as not having an elliptical from may be used to define a typical or average tissue color. Tissue color may, for example, be defined as one color or may be defined as a range of colors. In one example, average or typical tissue color may be defined as a varying parameter that may change, for example, in a defined way over the length of the GI tract, or over the length of a specific section in the GI tract, e.g. the colon. Content color may be defined in a similar manner. In one example, content color may be defined based on sample images taken, for example, from a database of images captured in one or mote volunteers. In another example, content color may be defined per patient. Content color may, for example, be defined as one color or may be defined as a range of colors. In one example, average or typical content color may be defined as a varying parameter that may change, for example, in a defined way over the length of the GI tract, or over the length of a specific section in the GI tract, e.g. the colon. In another example, the user, e.g. the health professional may, for example, mark areas in one or more image frames that may be used as reference tissue color and/or reference content colors. Other suitable methods of determining reference colors of tissue and content may be used. The identified elliptical forms may be compared to the defined tissue color and to the defined content color. In other examples the elliptical forms may be compared to other defined colors or to other colors. Color and size sorting may be based the probability that each ellipse identified is content, polyp, or neither. For example, if an identified elliptical area has a probability higher than a first threshold that it may be a polyp and has a probability lower than another threshold that it may be content; that identified elliptical area may be selected for the polyp category. In other examples, color or other identifying features to identify or classify a geometrical form as a bubble may be defined. Other suitable methods may be used for sorting defined forms.

Figure 3:
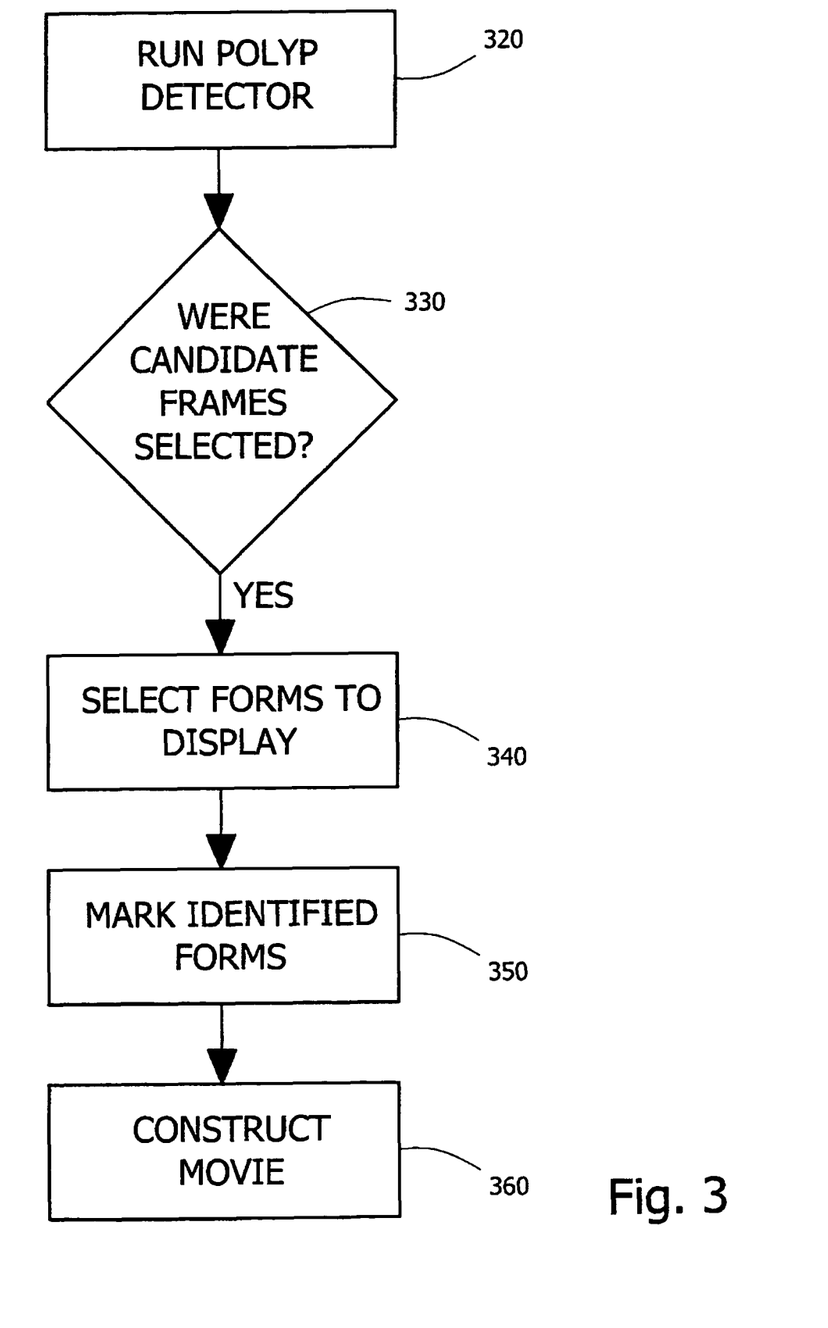
FIG. 3 is a flow chart describing a method for displaying selected image frames from an image stream according to embodiments of the present invention.

In block 240 ellipses classified as tissue maybe marked. In block 250 a score may be assigned to the frame based on the classifying. For example a score may be assigned to an image frame based on the number of forms categorized and/or classified as polyps in the image frame and the probability, for example the overall probability, that a polyp may have been correctly identified in the image frame. The classifying may be based on parameters such as color, size, and/or shape. Based on the score allotted, candidate image frames for polyp diagnosis may be selected (block 260). In one example, an image frame allotted a score above a defined threshold, may be marked as an image frame that may be a candidate for polyp diagnosis. Other image frames, e.g. subsequent image frames, may undergo screening in the similar manner described herein. Other operations or series of operations may be used In one embodiment of the present invention, a polyp detector may automatically select from an original image stream one or more candidate image frames for polyp diagnosis and a display unit may display the selected image frames for diagnosis by a health care professional. Reference is now made to FIG. 3 describing a method for displaying selected candidate image frames selected from an original image stream. In one embodiment of the present invention, polyp screening may be performed on a series of image frames included in an original image stream In other embodiments, polyp screening may be performed on a group of image frames selected from an original image stream. In one example, a group of image frames for polyp screening may be selected based on the location of interest, for example, polyp screening may be performed only on images captured in the colon. Other regions may be used for polyp screening. The polyp detector may be initiated and/or run to identify candidate image frames for polyp identification (block 320). In cases where candidate image frames were selected (block 330) a decision may be made as to which image frames to display (block 340). In one example, the decision may be based on the score assigned to each of the selected frames For example, image frames assigned scores in a defined range may be selected for display. Other suitable methods for selecting frames for display may be implemented In some embodiments of the present invention, identified forms may be marked (block 350), for example with an arrow pointing to the area, an enclosed shape encircling the area, or other suitable methods of marking an area in an image frame may be used. Selected image frames may be included in a subset image stream for display In block 360 a shortened movie, for example a polyp screening movie, may be constructed based on the subset image frame. The movie or streaming image frames may be shown or displayed to the health professional for diagnosis (block 370). The moving image stream may include a series of candidate image frames, typically still images, and may be displayed or stored as, for example, a subset image stream, a video, moving image, or movie. Other operations of series of operations may be used Polyp screening and image selection may be performed in teal time, or may be performed during the downloading procedure to the workstation 14 (FIG. 1), or at other suitable times or points in the imaging and/or screening procedures.

Figure 4A:
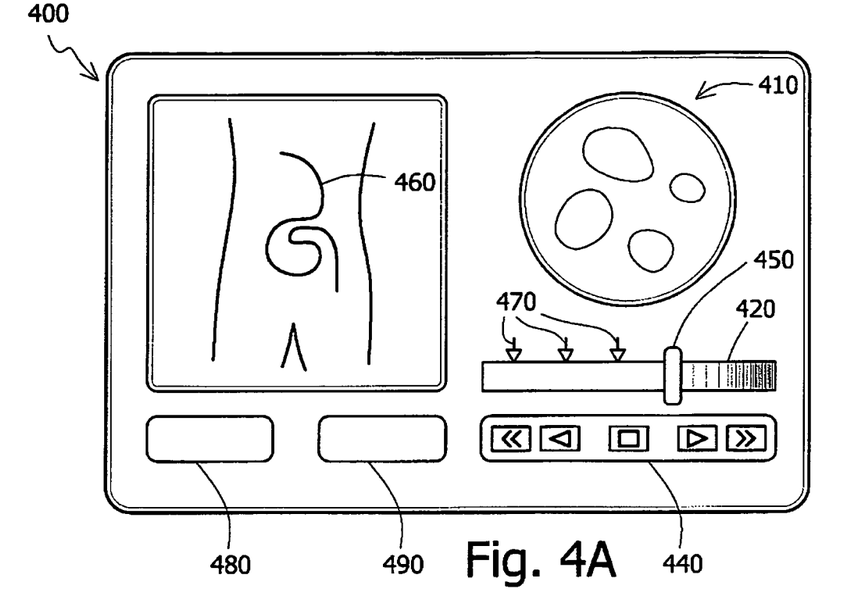
FIG. 4A shows a schematic graphical user interface (GUI) for use with an embodiment of the present invention.

Reference is now made to FIG. 4A showing schematic screen of a graphical user interface (GUI) that may be used, according to one embodiment, to display a polyp screening movie including candidate image frames selected for polyp identification The polyp screening movie may include image frames automatically selected by a polyp detector. Polyp screening movie window 410 may display a streaming display of image frames while an indicator 450 may advance to a position along a summarized graphical presentation bar 420 e.g. time/location bar that may indicate from where along the image stream the current frame displayed in movie window 410 may have been obtained. One or more image frames in movie window 410 may, for example, be marked to highlight areas in each frame that may potentially be a polyp form as may be described herein. A tracking curve 460 that may track the course of the imaging device may be shown. An indicator similar to indicator 450 may be used on the tracking curve to show correspondence with image frames displayed in window movie 410 and graphical presentation bar 420.

Summarized graphical presentation bar 420 may be similar to summarized graphical presentation bar described for example in US Patent Application Publication Number 20050075551, published on Apr. 7, 2005 which is assigned to the common assignee of the present application and incorporated herein by reference in its entirety or may be similar to other suitable graphical presentations. The position of indicator 450 along bat 420 may be controlled by user input to initiate image streaming in movie window 410 from a specified image frame in the image stream. Markers 470 may indicate from where along bar 420 candidate image frames may have been obtained. Control buttons 440 may be included in the GUI 400 and may allow a user to, for example, fast-forward, rewind, stop, play or reach the beginning or end of an image stream displayed in movie window 410. In one embodiment of the present invention, control buttons 440 may allow a user to choose to view image frames not selected as candidate image frames, for example, to view image frames that may appear in the original image frame directly before or after a candidate image frame. Polyp screening button 480 may allow a user to initiate the polyp screening procedure for example as described in FIG. 2 and FIG. 3 or to initiate streaming of the shortened polyp movie in movie window 410. In other examples, the automatic polyp screening may be initiated automatically or at a different point in the overall diagnostic procedure, e.g. during recording, downloading, and/or uploading of image data. In other embodiments of the present invention, one or more image frames may be shown concurrently in movie window 410.

A user or health professional may select one or more image frames from the movie window 410 to include in a report, e g diagnosis report. Markers 470 may be highlighted to indicate that a specific frame has been selected. Additional markers 470, marking non-candidate images may be added by the user. Clicking or otherwise indicating 'make report' button 490 may advance a user to a new screen that may show image frames that the user selected and provide a template for a user to prepare a diagnosis report.

Figure 4B:
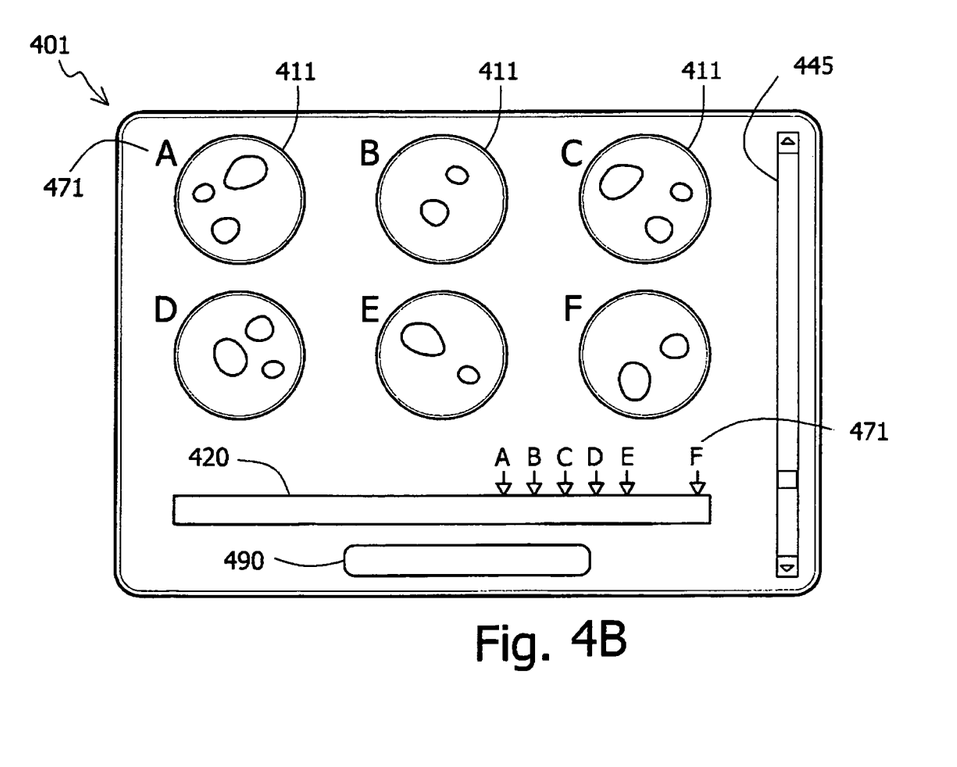
FIG. 4B shows a schematic graphical user interface (GUI) for use with an alternate embodiment of the present invention.

Reference is now made to FIG. 4B showing an alternate schematic screen of a GUI used to display one or more selected image frames according to one embodiment of the invention In one embodiment of the present invention, one or more image frames 411 selected by the polyp detector may be shown in screen 401, for example image frames 411 may be shown as thumbnails. The image frames 411 may include markings to locate polyps automatically detected by the polyp detector and/or detected by the health profession reviewing the images Markers 470 may indicate from where along bar 420 selected image frames may have been obtained. In one example, each of the image frames may be indexed and used to identify corresponding markers 470. A scroll bar 445 may be used to scroll down and/or update screen 401 to show more image frames 411 when not all the image frames 411 selected by polyp detector fit on a single screen. Selecting an image frame 411 by user input, for example by pointing with a mouse and clicking may initiate display of the selected image frame in a large size for example, for the purpose of user inspection. A user or health professional may select one or more image frames from the selected frames 411 to include in a report and may add markings to the image frames. Indices

471 may be highlighted, colored or otherwise marked to show them as user selected images One or more images frames 411 selected may be unselected. Choosing and/or clicking on make report button 490 may advance a user to a new screen that may show image frames that the user selected and may allow the user to prepare a diagnosis report or to prepare a referral to an additional diagnosis and/or treatment procedure.

Polyps may be one example of a morphologic feature and/or abnormality that may be detected and used for diagnosis. In other embodiments the method described herein may be used to detect other morphologic features. It will be appreciated by persons skilled in the art that the present invention is not limited to what has been particularly shown and described herein. Rather the scope of the present invention is defined only by the claims, which follow:

The invention claimed is:

1. A method to automatically screen for the presence of a polyp in a body lumen, said method comprising:
    capturing at least one image frame from within the body lumen using a swallowable autonomous imaging device;
    generating a gradient map of the at least one image frame;
    automatically identifying, using a processor and the generated gradient map, an elliptical form;
    comparing, using a processor, the color of the elliptical form to one or more predefined colors to differentiate between elliptical content and elliptical polyps;
    comparing, using a processor, the size of the elliptical form to a predetermined size parameter; and
    automatically classifying the elliptical form as content, polyp or neither in accordance with said color and size.

2. The method according to claim 1 comprising inserting an autonomous imaging device in-vivo.

3. The method according to claim 1 comprising tracking a location of where the at least one image frame was captured.

4. The method according to claim 1 comprising assigning a score to the at least one image frame wherein the score is based on the classifying.

5. The method according to claim 1 wherein the at least one image frame is an image stream.

6. The method according to claim 5 comprising:
    selecting candidate image frames from the image stream; and
    displaying the candidate image frames.

7. The method according to claim 6 comprising constructing a polyp screening movie wherein the polyp screening movie includes the candidate image frames.

8. The method according to claim 1 comprising:
    displaying the at least one image frame; and
    marking the elliptical form identified.

9. The method according to claim 1 comprising wherein the predefined colors are determined by defining a range of colors of typical tissue and a range of colors of typical content.

10. The method according to claim 9 wherein defining the range of colors of typical tissue per patient is performed according to the section of the body lumen in which the image frame appears.

11. A system to automatically screen for the presence of a polyp along a body lumen comprising:
    a swallowable imaging device to provide at least one image frame of the body lumen;
    a polyp detector to generate a gradient map of the at least one image frame, identify an elliptical form using the generated gradient map, compare the color of the elliptical form to a predefined color to differentiate between elliptical content and elliptical polyps, compare the size of the elliptical form to a predetermined size parameter, and to classify the elliptical form as content, polyp or neither in accordance with said color and size; and
    a display unit.

12. The system according to claim 11 wherein the image device provides a stream of image frames of the body lumen and wherein the polyp detector is to automatically select candidate image frames from the stream.

13. The system according to claim 12 comprising a processing unit wherein the processing unit is to construct a polyp screening movie from the candidate image frames selected by the polyp detector.

14. The system according to claim 12 wherein the display unit is to display candidate image frames selected by the polyp detector.

15. The system according to claim 11 wherein the polyp detector is included in the imaging device.

16. The system according to claim 11 wherein the polyp detector is included in an external receiving device wherein the external receiving device is to receive data from the imaging device.

17. The system according to claim 11 wherein the imaging device is an autonomous in-vivo device in the form of a capsule.

18. The system according to claim 17 comprising a tracking unit wherein the tracking unit is to track a location of the autonomous in-vivo imaging device within the body lumen.

* * * * *